United States Patent [19]

Dutta et al.

[11] 4,123,523

[45] Oct. 31, 1978

[54] ANALGESIC AND SEDATIVE POLYPEPTIDES

[75] Inventors: Anand S. Dutta; James J. Gormley; Christopher F. Hayward; John S. Morley; Nigel N. Petter; Gilbert J. Stacey, all of Macclesfield, England

[73] Assignee: Imperial Chemical Industries Limited, London, England

[21] Appl. No.: 803,233

[22] Filed: Jun. 3, 1977

[30] Foreign Application Priority Data

Jun. 21, 1976 [GB] United Kingdom ............... 25643/76
Oct. 28, 1976 [GB] United Kingdom ............... 44840/76

[51] Int. Cl.² .................... A61K 37/02; C07C 103/52
[52] U.S. Cl. ............................. 424/177; 260/112.5 R
[58] Field of Search .................. 424/177; 260/112.5 R

[56] References Cited

U.S. PATENT DOCUMENTS 4,038,222  7/1977  Li .......................................... 424/177

OTHER PUBLICATIONS

L. Graf, et al., FEBS Letters, 1976, 64, pp. 181–184.
D. H. Coy, et al., Biochem. and Biophys. Res. Commun., 73, 1976, pp. 632–637.
Pert, et al., Opiates and Endogenous Opioid Peptides, 1976, pp. 79–86.
Belluzzi, Proc. Natl. Acad. Sci. USA, 73, pp. 3308–3310, 1976.
Morgan, et al., Commun. J. Pharm. Pharmac., 1976, 28, pp. 660–661.
L. Terenius, et al., Biochem and Biophys. Res. Commun., 71, 1976, pp. 175–179.
Science, 194, pp. 330–332.
Biochem. and Biophys. Res. Commun., 73, 1976, pp. 632–638.

*Primary Examiner*—Delbert R. Phillips
*Attorney, Agent, or Firm*—Cushman, Darby & Cushman

[57] ABSTRACT

The disclosure relates to novel polypeptides which possess analgesic and sedative activity, to processes for their manufacture and to compositions containing them. Typical of the peptides disclosed is H-Tyr-D-Ala-Gly-Phe-Leu-Ala-Ile-Ile-Lys-Asn-Ala-Tyr-Lys-Lys-OH.

10 Claims, No Drawings

ANALGESIC AND SEDATIVE POLYPEPTIDES

This invention relates to polypeptides which possess analgesic and sedative properties.

It is known that residues 61-91 of the naturally-occuring lipolytic polypeptide hormone lipotropin (now known as the C-fragment of lipotropin, or β-endorphin) possesses analgesic properties when injected directly into the third ventricle of the cat. (A. F. Bradbury et al., Nature, 1976, 260, 793). It has now been found that linking the 61-65 sequence of β-endorphin, or variations thereof in which a D-amino-acid residue is substituted at position 62, with truncated fragments of the 66-91 sequence of progressively decreasing size leads initially to compounds having sedative activity, but only weak analgesic activity, when dosed intravenously, and then subsequently to compounds in which pronounced intravenous analgesic activity appears at the expense of sedative activity.

According to the invention there is provided a polypeptide of the formula:

  I in which A stands for D-Ala, D-Ser, D-Met or Gly; B stands for Leu or Met, E stands for a hydroxy or amino radical or for an alkoxy radical of 1 to 6 carbon atoms; and P stands for a peptide residue of the formula:

  II

  III

  IV

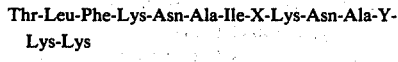  V

  VI in which X is Val or Ile and Y is Tyr or His; and the pharmaceutically-acceptable acid-addition salts thereof, and where the polypeptide of the formula I contains a free carboxy group, the pharmaceutically-acceptable base-addition salts thereof.

In the above formula I and throughout this specification, the amino-acid residues are designated by their standard abbreviations (Pure and Applied Chemistry, 1974, 40, 317-331). Where the configuration of a particular amino-acid is not designated, that amino-acid (apart from glycine which contains no asymmetric centre) has the natural L-configuration.

In the above formula I, a particular value for A is D-Ala, for B is Leu, for E is a hydroxy radical, for X is Ile and for Y is Tyr.

The following groups of compounds lie within the above definitions of the compound of the invention
  Those wherein P has the formula II, III, IV or V.
  Those wherein P has the formula VI.

The compounds in which A is D-Ala form a subgroup with the above groups, and within the first group and the subgroup lie those compounds in which P has the formula IV.

The preferred compound of the invention is that wherein A is D-Ala, B is Leu, E is a hydroxy radical and P has the formula IV given above in which X is Ile and Y is Tyr.

The polypeptide of the invention may be manufactured by methods known in themselves for the manufacture of chemically analogous compounds. Thus the following processes, A, B, P, E, X and Y having the meanings stated above, are provided as further features of the invention (a) the removal of one or more conventional peptide protecting groups from a protected polypeptide to give the compound of the formula I; or
(b) for those compounds in which E is an amino or alkoxy radical, reaction of the carboxylic acid having the formula I given above in which K is a hydroxy radical, or an activated derivative thereof, with ammonia or an alcohol of 1 to 6 carbon atoms.

In process (a) the deprotection process may involve removal from a resin used in solid-phase synthesis according to Merrifield (R. B. Merrifield, *Advances in Enzymology*, 1969, 32, 221) or alternatively may involve removal of one or more of the standard protecting groups employed in peptide chemistry (see for example M. Bodansky and M. A. Ondetti, "Peptide Synthesis", Interscience, New York, 1966, Chapter IV.

In process (b) a suitable activated derivative of the starting material is, for example, an ester or anhydride. In the case of the activated derivative, the reaction may be conducted by bringing the activated derivative into contact with ammonia or the appropriate alcohol in the presence of a diluent or solvent. In those cases in which the starting material is the free acid, the reaction with ammonia or the appropriate alcohol may be brought about by a standard peptide coupling reagent such as N,N'-dicyclohexylcarbodi-imide.

The starting materials for use in the processes of the invention may be prepared from known compounds by standard peptide coupling reactions, standard peptide protection reactions and standard peptide deprotection reactions well known to one skilled in this art. The starting materials are most conveniently prepared by Merrifield solid phase synthesis, for example as set out in the Examples.

As noted above, the compound of the formula I has analgesic and sedative activity in warm-blooded animals. The analgesic activity may be demonstrated in a standard test for detecting analgesic activity such as the mouse hot-plate test (Eddy and Leimbach, *J. Pharmac. Exp.Therap.*, 1953, 107, 385–393). This test is carried out as follows. Groups of three female mice each weighing 22 to 25 g. are used to test each compound. Each mouse is placed on a heated thermostatically-controlled copper surface at 56° C., and the time taken to react to the thermal stimulus (for example by licking its hind paws) is recorded. Normal reaction times are in the range 3 to 5 seconds.

Each of the three mice is then dosed intravenously with 100 mg./kg. of a solution of the test compound. At 5, 10 and 30 minutes after dosing, each mouse is again placed on the hot plate and its reaction time determined. If the mouse does not respond after 20 seconds, the mouse is removed from the hot plate. In this circumstance the compound is regarded as having maximum activity at this dose.

A compound producing a mean increase in reaction time of at least three seconds is regarded as active. An active compound is then retested at lower doses.

The compounds of the invention all display analgesic activity at or below 100 mg./kg. on this test without at the same time showing any obvious signs of toxicity.

Sedative activity may be demonstrated on a standard test such as the shock-induced aggression test in mice (Tedeschi, Tedeschi, Mucha, Cook, Mathis and Fellows, *J. Pharmac. Exp. Therap.*, 1959, 125, 28). The compounds of the invention in which P has the formula VI given above display sedative activity at or below an intravenous dose of 50 mg./kg. on this test.

The compounds of the invention which display pronounced sedative activity, but only weak analgesic activity, are those of the formula I above in which P has the formula VI. The compounds of the invention which display pronounced analgesic activity, accompanied by varying degrees of sedative activity, are those of the formula I above in which P has the formula II, III, IV or V.

According to a further feature of the invention there is provided a pharmaceutical composition which comprises as active ingredient the polypeptide derivative of the invention in association with a non-toxic pharmaceutically-acceptable diluent or carrier.

The pharmaceutical composition may be, for example, in a form suitable for parenteral administration, for which purposes it may be formulated by means known to the art into the form of sterile injectable aqueous or oily solutions or suspensions.

The pharmaceutical composition of the invention may also contain, in addition to the polypeptide derivative, one or more known drugs selected from analgesic agents, for example aspirin, paracetamol, phenacetin, codeine, pethidine, and morphine, anti-inflammatory agents, for example naproxen, indomethacin and ibuprofen, neuroleptic agents such as chlorpromazine, prochlorperazine, trifluoperazine and haloperidol and other sedative drugs and tranquillisers such as chlordiazepoxide, phenobarbitone and amylobarbitone.

A preferred pharmaceutical composition of the invention is one suitable for intravenous, intramuscular or subcutaneous injection, for example a sterile aqueous solution containing between 1 and 50 mg./ml. of active ingredient.

The pharmaceutical composition of the invention will normally be administered to man for the treatment or prevention of pain or to produce sedation at such a dose that each patient receives an intramuscular or subcutaneous dose of between 2 and 150 mg. of active ingredient or an intravenous dose of between 1 and 100 mg. of active ingredient.

The composition may be administered according to a regime determined by the biological half-life of the polypeptide derivative, for example at intervals of from 0.5 to 4 times the biological half-life, for example 2 to 6 times per day. The composition of the invention will be of particular use in alleviating the pain experienced during and immediately after a surgical operation, and in this situation will normally be administered during the operation itself and in the immediate post-operative period.

The injectable composition of the invention may be administered by slug dose, either directly into the site of injection or into a previously-placed intravenous infusion arrangement, or it may be administered more slowly in dilute solution as a component of the intravenous infusion fluid.

The invention is illustrated, but not limited, by the following Examples:-

In the following Examples $R_f$ refers to ascending thin layer chromatography on silica gel plates (Kieselgel G). The solvent systems used in this chromatography were butan-1-ol/acetic acid/water (4:1:5 v/v) ($R_fA$), butan-1-ol/acetic acid/water/pyridine (15:3:12:10 v/v) ($R_fB$) and butan-2-ol/3% w/v aqueous ammonium hydroxide (3:1 v/v) ($R_fC$). In all cases, plates were examined under U.V. light and treated with fluorescamine, ninhydrin, and chlorine-starch-iodide reagents. Unless otherwise stated, the quoting of an $R_f$ implies that a single spot was revealed by these methods.

Acid hydrolysates of all final products described in this specification were prepared by heating the peptide with 6N-hydrochloric acid containing 1% w/v phenol in a sealed evacuated tube for 16 hours at 110° C. The amino-acid composition of each hydrolysate was determined with a LoCarte Amino-acid Analyser.

In the Examples the following contractions are used:-
DNP — 2,4-dinitrophenyl
TFA — trifluoroacetic acid
TEA — triethylamine
BOC — t-butyloxycarbonyl
DCCI — N,N'-dicyclohexylcarbodi-imide
DMF — dimethylformamide
ONP — p-nitrophenoxy
mBrBzl — meta-bromobenzyl
Bzl — benzyl
'Sephadex' and 'Biorex' are trade marks.

EXAMPLE 1

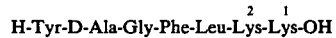
H-Tyr-D-Ala-Gly-Phe-Leu-Lys-Lys-OH

N-t-butyloxycarbonyl-O-t-butyl-L-tyrosyl-D-alanylglycyl-L-phenylalanyl-L-leucyl-N-2,4-dichlorobenzyloxycarbonyl-L-lysyl-N$^\epsilon$-2,4-dichlorobenzyloxycarbonyl-L-lysyl-polystyrene resin (1 g.) was treated in vacuo with liquid anhydrous hydrogen fluoride (15 ml.) and anisole (1.5 ml.) at 0° C. for 1 hour. The hydrogen fluoride and anisole were then removed as quickly as possible by evaporation under reduced pressure at 0° C. and the residue was extracted with ether and then with 10% v/v aqueous acetic acid. The aqueous acetic acid extract was freeze-dried and the resulting crude peptide purified by column chromatography using G-15 'Sephadex' in 5% v/v aqueous acetic acid (2 passages). The product had the following properties:- $R_fA$ 0.18, $R_fB$ 0.54, $R_fC$ 0.06, paper electrophoresis at pH 2.1 single discrete spot at $R_f$ 2.33 with respect to $\epsilon$-DNP-Lys.

Dansylation products: as expected ($\epsilon$-Lys, bis-Tyr, O-Tyr)

Amino-acid analysis: Gly 1.00 (1); Ala 0.98 (1); Leu 1.00 (1); Tyr 0.97 (1); Phe 0.99 (1); Lys 2.08 (2).

The protected 7-member polypeptide-polystyrene resin used as starting material may be obtained as follows:-

Solid phase synthesis

Chlorinated polystyrene resin (Lab. Systems Inc. Batch No. LS601) (6 g., chlorine content 0.75 mmole/g., 1% cross-linked with divinylbenzene) was heated under reflux in ethanol (40 ml.) in a 250 ml. round bottom flask with N$^\alpha$-t-butyloxycarbonyl-N$^\epsilon$-2,4-dichlorobenzyloxycarbonyl-L-lysine (2.03 g., 4.5 mmole) and triethylamine (0.56 ml., 4.05 mmole) for 20 hours. The resin was filtered and washed with ethanol, methanol and methylene chloride. Fragmented particles of resin were removed by suspending the total resin in methylene chloride in a separating funnel and running off the fine suspension underlying the unfragmented resin layer. The resin was then found to be substituted to the extent of 0.20 mmole of $N^\alpha$-t-butyloxycarbonyl-$N^\epsilon$-2,4-dichlorobenzyloxycarbonyl-L-lysine per gram of resin by amino-acid analysis (Resin I).

5 g. Resin I was transferred to the reaction vessel (10 g. capacity) of a Beckman Model 990 Peptide Synthesiser, and the following programmed operations were then carried out:-
1. Wash with $CH_2Cl_2$ for 1 minute : 3 times
2. Prewash with 50% v/v TFA in $CH_2Cl_2$ for 1 minute : once
3. Deprotect with 50% v/v TFA in $CH_2Cl_2$ for 30 minute : once
4. Wash with $CH_2Cl_2$ for 1 minute : 5 times
5. Wash with i-PrOH for 1 minute : twice
6. Wash with $CH_2Cl_2$ for 1 minute : 3 times
7. Prewash with 10% v/v TEA in $CH_2Cl_2$ for 1 minute : once
8. Neutralise with 10% v/v TEA in $CH_2Cl_2$ for 5 minutes : once
9. Wash with $CH_2Cl_2$ for 1 minute : 3 times
10. Wash with i-PrOH for 1 minute : twice
11. Wash with $CH_2Cl_2$ for 1 minute : 3 times
12. Add $N^\alpha$-BOC-$N^\epsilon$-2,4-dichlorobenzyloxycarbonyl-L-lysine (2.5 equivalents based on initial lysine incorporation) in $CH_2Cl_2$ and stir for 5 minutes.
13. Add DCCI (2.5 equivalents) in $CH_2Cl_2$ and couple for 1 hour.
14. Wash with $CH_2Cl_2$ for 1 minute : 4 times
15-21 As operations 5-11.
22. Add $N^\alpha$-BOC-$N^\epsilon$-2,4-dichlorobenzyloxycarbonyl-L-lysine (2.5 equivalents) in DMF-$CH_2Cl_2$ and stir for 5 minutes.
23. Add DCCI (2.5 equivalents) in $CH_2Cl_2$ and couple for 3 hours.
24. As operation 14

After operation 24 all but 1 g. of $N^\alpha$-BOC-$N^\epsilon$-2,4-dichlorobenzyloxycarbonyl-L-lysyl-$N^\epsilon$-2,4-dichlorobenzyloxycarbonyl-L-lysylpolystyrene resin (Resin II) was removed from the reaction vessel.

In the case of incorporation of the final pentapeptide fragment BOC-Tyr(Bu$^t$)-D-Ala-Gly-Phe-Leu-OH (Starting Material No. 161 in Example 94 in U.K. Patent Application No. 14362/76), this fragment, 1-hydroxybenzotriazole and N-methylmorpholine (1.5 equivalents each) were used in operations 12 and 22, DMF (1 ml.) was used to dissolve the 1-hydroxybenzotriazole in operation 12 and stirring was continued for 10 minutes in operations 12 and 22 and for 24 hours in operations 13 and 23.

The final protected 7 member polypeptide coupled to the resin was washed with dimethylformamide, methylene chloride and isopropanol and dried in vacuo.

EXAMPLE 2

H-Tyr-D-Ala-Gly-Phe-Leu-Asn-Ala-Tyr-Lys-Lys-OH

N-t-Butyloxycarbonyl-O-t-butyl-L-tyrosyl-D-alanylglycyl-L-phenylalanyl-L-leucyl-L-asparaginyl-L-alanyl-O-m-bromobenzyl-L-tyrosyl-$N^\epsilon$-2,4-dichlorobenzyloxycarbonyl-L-lysyl-$N^\epsilon$-2,4-dichlorobenzyloxycarbonyl-L-lysyl-polystyrene resin (1 g.) was treated with liquid anhydrous hydrogen fluoride and anisole, and the product purified, as described in the first part of Example 1. The product had the following properties:- $R_fA$ 0.19, $R_fB$ 0.59, $R_fC$ 0.05, paper electrophoresis at pH 2.1 single discrete spot at $R_f$ 1.89 with respect to $\epsilon$-DNP-Lys.

Dansylation products: as expected ($\epsilon$-Lys, bis-Tyr, O-Tyr)

Amino-acid analysis: Asp 0.99 (1); Gly 1.00 (1); Ala 1.99 (2); Leu 0.98 (1); Tyr 1.96 (2); Phe 0.94 (1); Lys 2.15 (2).

The protected 10 member polypeptide-polystyrene resin used as starting material may be obtained as follows:-

Solid phase synthesis 4 g. Resin II (Example 1) was transferred to the reaction vessel and further amino-acids were then incorporated into the resin by, in each case, repeating the 24 operations used in Example 1, but using the appropriate BOC-amino-acid or BOC-amino-acid derivative in stages 12 and 22 in place of $N^\alpha$-BOC-$N^\epsilon$-2,4-dichlorobenzyloxycarbonyl-L-lysine. When Asn (position 5) was being incorporated, solutions of BOC-Asn-ONP (5 equivalents) and 1-hydroxybenzotriazole (5 equivalents) in DMF were used in operations 12 and 22 and stirring was continued for 4 hours in operation 12 and for 8 hours in operation 22; in this case operations 13 and 23 are changed to:- Wash with DMF for 1 minute : 4 times.

After incorporation of Asn (position 5)(operation 24) all but 1 g. of the resin (Resin III) was removed from the reaction vessel. The final pentapeptide fragment was incorporated as in Example 1.

The BOC-amino-acid or BOC-amino-acid derivatives used and the order in which they were incorporated were as follows:-
BOC-Tyr(m-BrBzl)-OH
BOC-Ala-OH
BOC-Asn-ONP
BOC-Tyr(Bu$^t$)-D-Ala-Gly-Phe-Leu-OH The final protected 10 member polypeptide coupled to the resin was washed with dimethylformamide, methylene chloride and isopropanol and dried in vacuo.

EXAMPLE 3

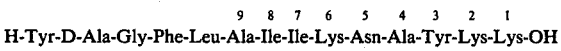
H-Tyr-D-Ala-Gly-Phe-Leu-Ala-Ile-Ile-Lys-Asn-Ala-Tyr-Lys-Lys-OH

N-t-Butyloxycarbonyl-O-t-butyl-L-tyrosyl-D-alanylglycyl-L-phenylalanyl-L-leucyl-L-alanyl-L-isoleucyl-L-isoleucyl-$N^\epsilon$-2,4-dichlorobenzyloxycarbonyl-L-lysyl-L-asparaginyl-L-alanyl-O-m-bromobenzyl-L-tyrosyl-$N^\epsilon$-2,4-dichlorobenzyloxycarbonyl-L-lysyl-$N^\epsilon$-2,4-dichlorobenzyloxycarbonyl-L-lysyl-polystyrene resin (1 g.) was treated with liquid anhydrous hydrogen fluoride and anisole and the reaction mixture worked up as described in the first part of Example 1. The product was purified by column chromatography using
(a) G-15 'Sephadex' in 5% v/v aqueous acetic acid
(b) G-25 'Sephadex' in 5% v/v aqueous acetic acid
(c) 'Biorex' 70 (carboxylic carbon exchange resin) in water with increasing strength of aqueous acetic acid (up to 25% v/v aqueous acetic acid).

The product had the following properties:- $R_fB$ 0.55
Dansylation products: as expected ($\epsilon$-Lys, bis-Tyr, O-Tyr)
Amino-acid analysis: Asp 0.99 (1); Gly 0.96 (1); Ala 2.92 (2); Ile* 1.35 (2); Leu 1.04 (1); Tyr 2.06 (2); Phe 1.07 (1); Lys 3.00 (3).
* Ile-Ile bond is resistant to 16 hour hydrolysis in 6N.HCl/phenol.

The protected 14 member polypeptide-polystyrene resin used as starting material may be obtained as follows:-

Solid phase synthesis 3 g. Resin III (Example 2) was transferred to the reaction vessel and further amino-acids were incorporated into the resin by, in each case, repeating the 24 operations described in Example 1 but using the appropriate BOC-amino-acid or BOC-amino-acid derivative in operations 12 and 22 in place of $N^\alpha$-BOC-$N^\epsilon$-2,4-dichlorobenzyloxycarbonyl-L-lysine.

After incorporation of Ile (position 7) (operation 24), the following acetylation procedure was carried out:-
25. Wash with i-PrOH for 1 minute : twice
26. Wash with $CH_2Cl_2$ for 1 minute : 3 times
27. Prewash with 10% v/v TEA in $CH_2Cl_2$ for 1 minute : once
28. Neutralise with 10% v/v TEA in $CH_2Cl_2$ for 5 minutes : once
29. Wash with $CH_2Cl_2$ for 1 minute : 3 times
30. Wash with i-PrOH for 1 minute : twice
31. Wash with $CH_2Cl_2$ for 1 minute : 3 times
32. Add a pre-equilibrated (stood for 30 minutes) and filtered mixture of
DCCI (2 equivalents based on initial lysine incorporation)
Acetic anhydride(50 equivalents)
TEA (2 equivalents) in $CH_2Cl_2$ (20 ml.) : Stir for 2 hours.
33. Wash with $CH_2Cl_2$ for 1 minute : 4 times After incorporation of Ile (position 8) (operation 24) the above acetylation procedure was carried out. After incorporation of Ala (position 9) (operation 24), all but 1 g. of the resin (Resin IV) was removed from the reaction vessel. The final pentapeptide fragment was incorporated as in Example 1.

The BOC-amino-acid or BOC-amino-acid derivatives used and the order in which they were incorporated were as follows:-
$N^\alpha$-BOC-$N^\epsilon$-2,4-dichlorobenzyloxycarbonyl-L-lysine
BOC-Ile-OH
BOC-Ile-OH
BOC-Ala-OH
BOC-Tyr(Bu$^t$)-D-Ala-Gly-Phe-Leu-OH The final protected 14 member polypeptide coupled to the resin was washed with dimethylformamide, methylene chloride and isopropanol and dried in vacuo.

EXAMPLE 4

14 13 12 11 10 9 8 7 6 5 4 3 2 1
H-Tyr-D-Ala-Gly-Phe-Leu-Thr-Leu-Phe-Lys-Asn-Ala-Ile-Ile-Lys-Asn-Ala-Tyr-Lys-Lys-OH

N-t-Butyloxycarbonyl-O-t-butyl-L-tyrosyl-D-alanyl-glycyl-L-phenylalanyl-L-leucyl-O-benzyl-L-threonyl-L-leucyl-L-phenylalanyl-$N^\epsilon$-2,4-dichlorobenzyloxycarbonyl-L-lysyl-L-asparaginyl-L-alanyl-L-isoleucyl-L-isoleucyl-$N^\epsilon$-2,4-dichlorobenzyloxycarbonyl-L-lysyl-L-asparaginyl-L-alanyl-O-m-bromobenzyl-L-tyrosyl-$N^\epsilon$-2,4-dichlorobenzyloxycarbonyl-L-lysyl-$N^\epsilon$-2,4-dichlorobenzyloxycarbonyl-L-lysyl-polystyrene resin (1 g.) was treated with liquid anhydrous hydrogen fluoride and anisole and the reaction mixtutre worked up as described in the first part of Example 1. The product was purified by column chromatography using
(a) G-15 'Sephadex' in 5% v/v aqueous acetic acid
(b) G-25 'Sephadex' in 5% v/v aqueous acetic acid
(c) 'Biorex' 70 (carboxylic carbon exchange resin) in water with increasing strength of aqueous acetic acid (up to 25% v/v aqueous acetic acid).

The product had the following properties:- $R_fA$ 0.21, $R_fB$ 0.56.
Dansylation products: as expected ($\epsilon$-Lys, bis-Tyr, O-Tyr)
Amino-acid analysis: Asp 2.00 (2); Thr 0.94 (1); Gly 0.95 (1); Ala 3.00 (3); Ile* 1.24 (2); Leu 2.04 (2); Tyr 1.98 (2); Phe 2.05 (2); Lys 3.97 (4).
*Ile-Ile bond is resistant to 16 hour hydrolysis in 6N.HCl/phenol.

The protected 19 member polypeptide-polystyrene resin used as a starting material may be contained as follows:-

Solid phase synthesis 2 g. Resin IV Example 3) was transferred to the reaction vessel and further amino-acids were incorporated into the resin by, in each case, repeating the 24 operations described in Example I but using the appropriate BOC-amino-acid or BOC-amino-acid derivative in stages 12 and 22 in place of $N^\alpha$-BOC-$N^\epsilon$-2,4-dichlorobenzyloxycarbonyl-L-lysine. After incorporation of Thr (position 14) the acetylation procedure described in operations 25-33 in Example3 was carried out. After incorporation of Thr (position 14) and subsequent acetylation (operation 33), all but 1 g. of the resin (Resin V) was removed from the reaction vessel. The final pentapeptide fragment was incorporated as in Example 1.

The BOC-amino-acid or BOC-amino-acid derivatives used and the order in which they were incorporated were as follows:-
BOC-Asn-ONP
$N^\alpha$-BOC-$N^\epsilon$-2,4-dichlorobenzyloxycarbonyl-L-lysine
BOC-Phe-OH
BOC-Leu-OH
BOC-Thr(Bzl)-OH
BOC-Tyr(Bu$^t$)-D-Ala-Gly-Phe-Leu-OH The final protected 19 member polypeptide coupled to the resin was washed with dimethylformamide, methylene chloride and isopropanol and dried in vacuo.

EXAMPLE 5

20 19 18 17 16 15 14 13 12 11 10 9 8 7 6 5 4 3 2 1
H-Tyr-D-Ala-Gly-Phe-Leu-Ser-Gln-Thr-Pro-Leu-Val-Thr-Leu-Phe-Lys-Asn-Ala-Ile-Ile-Lys-Asn-Ala-Tyr-Lys-Lys-OH

N-t-Butyloxcarbonyl-O-t-butyl-L-tyrosyl-D-alanylglycyl-L-phenylalanyl-L-leucyl-O-benzyl-L-seryl-L-glutaminyl-O-benzyl-L-threnonyl-L-prolyl-L-leucy-L-valyl-O-benzyl-L-threonyl-L-leucyl-L-phenylalanyl-$N^\epsilon$-2,4-dichlorobenzyloxycarbonyl-L-lysyl-L-asparaginyl-L-alanyl-L-isoleucyl-L-isoleucyl-$N^\epsilon$-2,4- dichlorobenzyloxycarbonyl-L-lysyl-L-asparaginyl-L-alanyl-O-m-bromobenzyl-L-tyrosyl-N$^\epsilon$-2,4-dichlorobenzyloxycarbonyl-L-lysyl-N$^\epsilon$-2,4-dichlorobenzyloxycarbonyl-L-lysyl-polystyrene resin (1 g.) was treated with liquid anhydrous hydrogen fluoride and anisole and the reaction mixture worked up as described in the first part of Example 1. The product was purified by column chromatography using (a) G-15 'Sephadex' in 5% v/v aqueous acetic acid
(b) G-25 'Sephadex' in 5% v/v aqueous acetic acid
(c) 'Biorex' 70 (carboxylic carbon exchange resin) in water with increasing strength of aqueous acetic acid (up to 25% v/v aqueous acetic acid).

The product had the following properties:- $R_fB$ 0.56. Dansylation products: as expected ($\epsilon$-Lys, bis-Tyr, O-Tyr)
Amino-acid analysis: Asp 2.16 (2); Thr 1.64 (2); Ser 0.70 (1); Glu 0.80 (1); Gly 0.70 (1); Ala 3.06 (3); Val 0.91 (1); Ile* 1.27 (2); Leu 3.02 (3); Tyr 1.74 (2); Phe 1.80 (2); Lys 4.58 (4).

* Ile-Ile bond is resistant to 16 hour hydrolysis in 6N.HCl/phenol.

The protected 25 member polypeptide-polystyrene resin used as a starting material may be obtained as follows:-

Solid phase synthesis 1 g. Resin V (Example 4) was transferred to the reaction vessel and further amino-acids were incorporated into the resin by, in each case, repeating the 24 operations described in Example 1 but using the appropriate BOC-amino-acid or BOC-amino-acid derivative in operations 12 and 22 in place of N$^\alpha$-BOC-N$^\epsilon$-2,4-dichlorobenzyloxycarbonyl-L-lysine. When Gln (position 19) was being incorporated, solutions of BOC-Gln-ONP (5 equivalents) and 1-hydroxybenzotriazole (5 equivalents) in DMF were used in operations 12 and 22 and stirring was continued for 4 hours in operation 12 and for 8 hours in operation 22; in this case operations 13 and 23 are changed to:- Wash with DMF for 1 minute : 4 times.

After incorporation of Val (position 15) and Ser (position 20) acetylation procedures were carried out (as in operations 25-33 in Example 3).

The final pentapeptide fragment was incorporated as in Example 1. The BOC-amino-acid or BOC-amino-acid derivatives used and the order in which they were incorporated were as follows:-

BOC-Val-OH
BOC-Leu-OH
BOC-Pro-OH
BOC-Thr(Bzl)-OH
BOC-Gln-ONP
BOC-Ser(Bzl)-OH
BOC-Tyr(Bu$^t$)-D-Ala-Gly-Phe-Leu-OH

The final protected 25 member polypeptide coupled to the resin was washed with dimethylformamide, methylene chloride, isopropanol and dried in vacuo.

What we claim is:-

1. A polypeptide of the formula:-

H-Tyr-A-Gly-Phe-B-P-E    I in which A is selected from the group consisting of D-Ala, D-Ser, D-Met and Gly; B is selected from the group consisting of Leu and Met, E is selected from the group consisting of a hydroxy and amino radical and an alkoxy radical of 1 to 6 carbons; and P is a peptide residue selected from those of the formula:-

| Lys-Lys | II |
| Asn-Ala-Y-Lys-Lys | III |
| Ala-Ile-X-Lys-Asn-Ala-Y-Lys-Lys | IV |
| Thr-Leu-Phe-Lys-Asn-Ala-Ile-X-Lys-Asn-Ala-Y-Lys-Lys | V | and

Ser-Gln-Thr-Pro-Leu-Val-Thr-Leu-Phe-Lys-Asn-Ala-Ile-X-Lys-Asn-Ala-Y-Lys-Lys    VI in which X is Val or Ile and Y is Tyr or His; and the pharmaceutically-acceptable acid-addition salts thereof, and where the polypeptide of the formula I contains a free carboxygroup, the pharmaceutically-acceptable base-addition salts thereof.

2. A polypeptide as claimed in claim 1 in which A is D-Ala, B is Leu, E is a hydroxy radical, X is Ile and Y is Tyr.

3. A polypeptide as claimed in claim 1 in which P is a peptide residue selected from those of the formula II, III, IV and V given in claim 1.

4. A polypeptide as claimed in claim 1 in which P has the formula VI given in claim 1.

5. A polypeptide as claimed in claim 1 in which A is D-Ala.

6. A polypeptide as claimed in claim 1 in which P has the formula IV given in claim 1.

7. A polypeptide as claimed in claim 1 in which A is D-Ala, B is Leu, E is a hydroxy radical and P has the formula IV given in claim 1 in which X is Ile and Y is Tyr.

8. A pharmaceutical composition which comprises as active ingredient an effective amount of a polypeptide as claimed in claim 1 in association with a major amount of a non-toxic pharmaceutically-acceptable diluent or carrier.

9. A method of producing analgesia in warm-blooded animals including man which comprises administering an analgesically-effective amount of a polypeptide as claimed in claim 1.

10. A method of producing sedation in warm-blooded animals including man which comprises administering a sedatively-effective amount of a polypeptide as claimed in claim 4.

* * * * *